United States Patent
Degorce et al.

(10) Patent No.: US 6,632,624 B1
(45) Date of Patent: Oct. 14, 2003

(54) HUMAN CHROMOGRANIN A (CGA) IMMUNOLOGIC ASSAY, ANTIBODIES, REAGENTS AND KITS FOR SAID ASSAY

(75) Inventors: François Degorce, Saint Privat de Champclos (FR); Laurent Bellanger, Cabrieres D'Avignon (FR); Dominique Aunis, Strasbourg (FR)

(73) Assignee: CIS bio International, Saclay (FR)

(*) Notice: Subject to any disclaimer, the term of this patent is extended or adjusted under 35 U.S.C. 154(b) by 0 days.

(21) Appl. No.: 09/700,387

(22) PCT Filed: May 12, 1999

(86) PCT No.: PCT/FR99/01141

§ 371 (c)(1),
(2), (4) Date: Apr. 2, 2001

(87) PCT Pub. No.: WO99/58980

PCT Pub. Date: Nov. 18, 1999

(30) Foreign Application Priority Data

May 14, 1998 (FR) .............................................. 98 06101

(51) Int. Cl.[7] .................... G01N 35/542; G01N 33/533; G01N 33/537

(52) U.S. Cl. ...................... 435/7.92; 435/7.1; 435/7.21; 435/7.93; 435/7.95; 436/172; 436/800; 436/536; 436/546

(58) Field of Search ................................. 435/7.1, 7.21, 435/7.93, 7.95, 7.92; 436/172, 800, 536, 546

(56) References Cited

U.S. PATENT DOCUMENTS 4,758,522 A 7/1988 O'Connor
5,512,493 A * 4/1996 Mathis et al. ............... 436/537

FOREIGN PATENT DOCUMENTS

EP 0 321 353 6/1989
EP 0 449 269 10/1991
WO WO 92/01225 1/1992

OTHER PUBLICATIONS

Corti et al. Antigenic regions of human Chromogranin A and their topographic relationships with structure/functional domains Eur. J. Biochem. (1996) 253: 275–280.*

Koppert et al. A monoclonal antibody–based enzyme immunoassay for fibrin degradation products in plasma Thrombosis and Haemostasis (1988) 59: 310–315.*

Francois Degorce, et al., 24th Meeting of the International Society for Oncodevelopmental Biology and Medicine on the Interdependence of Tumor Biology and Clinical Oncology, vol. 18, No. Suppl. 1, p. 112, "Selection of Monoclonal Antibodies for the Measurement of Chromogranin A by Sandwich Assay", 1997.

David S. Konecki, et al., The Journal of Biological Chemistry, vol. 262, No. 35, pp. 17026–17030, "The Primary Structure of Human Chromogranin A and Pancreastatin", Dec. 15, 1987.

A. Corti, et al., British Journal of Cancer, vol. 73, pp. 924–932, "Characterisation of Circulating Chromogranin A in Human Cancer Patients", 1996.

Unni Syversen, et al., Acta Oncologica, vol. 32, No. 2, pp. 161–165, "Chromogranin A and Pancreastatin–Like Immunoreactivity in Serum of Gastrinoma Patients", 1993.

(List continued on next page.)

*Primary Examiner*—Long V. Le
*Assistant Examiner*—Changhwa Jacob Cheu
(74) *Attorney, Agent, or Firm*—Oblon, Spivak, McClelland, Maier & Neustadt, P.C.

(57) ABSTRACT

The invention pertains to an immunoassay, and a kit for said assay, in which at least one monoclonal antibody or polyclonal antibody specifically binds to an epitope corresponding to amino acids 145 to 234 of human chromogranin A.

21 Claims, 7 Drawing Sheets

OTHER PUBLICATIONS

G. Köhler, et al., Nature, vol. 256, pp. 495–497, "Continuous Cultures of Fused Cells Secreting Antibody of Predefined Specificity", Aug. 7, 1975.

Daniel T. O'Connor, et al., The New England Journal of Medicine, vol. 311, No. 12, pp. 764–770, "Radioimmunoassay of Chromogranin A in Plasma as a Measure of Exocytotic Sympathoadrenal Activity in Normal Subjects and Patients with Pheochromocytoma", Sep. 20, 1984.

Patrick H. O'Farrell, The Journal of Biological Chemistry, vol. 250, No. 10, pp. 4007–4021, "High Resolution Two–Dimensional Electrophoresis of Proteins", 1975.

M.–F. Bader, et al., Neuroscience, vol. 8, No. 1, pp. 165–181, "The 97–KD α–Actinin–Like Protein in Chromaffin Granule Membranes from Adrenal Medulla: Evidence for Localization on the Cytoplasmic Surface and for Binding to Actin Filaments", 1983.

Laurent Taupenot, et al., Regulatory Peptides, vol. 56, pp. 71–88, "Recombinant Human Chromogranin A: Expression, Purification and Characterization of the N–Terminal Derived Peptides", 1995.

Yannick Goumon, et al., Eur. J. Biochem., vol. 235, pp. 516–525, "The C–Terminal Bisphosphorylated Proenkephalin–A–(209–237)–Peptide from Adrenal Medullary Chromaffin Granules Possesses Antibacterial Activity", 1996.

Evelyne Lopez, et al., Clinical Chemistry, vol. 39, No. 2, pp. 196–201, "Europium (III) Trisbipyridine Cryptate Label for Time–Resolved Fluorescence Detection of Polymerase Chain Reaction Products Fixed on a Solid Support", 1993.

Gérard Mathis, Clinical Chemistry, vol. 39, No. 9, pp. 1953–1959, "Rare Earth Cryptates and Homogeneous Fluroimmunoassays with Human Sera", 1993.

David G. Munoz, Laboratory Investigation, vol. 64, No. 6, pp. 826–832, "Chromogranin A–Like Immunoreactive Neurites are Major Constituents of Senile Plaques", 1991.

* cited by examiner

```
Leu Pro Val Asn Ser Pro Met Asn Lys Gly Asp Thr Glu Val Met
                 5               10               15
Lys Cys Ile Val Glu Val Ile Ser Asp Thr Leu Ser Lys Pro Ser
                20               25               30
Pro Met Pro Val Ser Gln Glu Cys Phe Glu Thr Leu Arg Gly Asp
                35               40               45
Glu Arg Ile Leu Ser Ile Leu Arg His Gln Asn Leu Leu Lys Glu
                50               55               60
Leu Gln Asp Leu Ala Leu Gln Gly Ala Lys Glu Arg Ala His Gln
                65               70               75
Gln Lys Lys His Ser Gly Phe Glu Asp Glu Leu Ser Glu Val Leu
                80               85               90
Glu Asn Gln Ser Ser Gln Ala Glu Leu Lys Glu Ala Val Glu Glu
                95               100              105
Pro Ser Ser Lys Asp Val Met Glu Lys Arg Glu Asp Ser Lys Glu
                110              115              120
Ala Glu Lys Ser Gly Glu Ala Thr Asp Gly Ala Arg Pro Gln Ala
                125              130              135
Leu Pro Glu Pro Met Gln Glu Ser Lys Ala Glu Gly Asn Asn Gln
                140              145              150
Ala Pro Gly Glu Glu Glu Glu Glu Glu Glu Ala Thr Asn Thr
                155              160              165
His Pro Pro Ala Ser Leu Pro Ser Gln Lys Tyr Pro Gly Pro Gln
                170              175              180
Ala Glu Gly Asp Ser Glu Gly Leu Ser Gln Gly Leu Val Asp Arg
                185              190              195
Glu Lys Gly Leu Ser Ala Glu Pro Gly Trp Gln Ala Lys Arg Glu
                200              205              210
Glu Glu Glu Glu Glu Glu Glu Ala Glu Ala Gly Glu Glu Ala
                215              220              225
Val Pro Glu Glu Glu Gly Pro Thr Val Val Leu Asn Pro His Pro
                230              235              240
```

FIG. 1A

```
Ser Leu Gly Tyr Lys Glu Ile Arg Lys Gly Glu Ser Arg Ser Glu
                245                 250                 255
Ala Leu Ala Val Asp Gly Ala Gly Lys Pro Gly Ala Glu Glu Ala
                260                 265                 270
Gln Asp Pro Glu Gly Lys Gly Glu Gln Glu His Ser Gln Gln Lys
                275                 280                 285
Glu Glu Glu Glu Glu Met Ala Val Val Pro Gln Gly Leu Phe Arg
                290                 295                 300
Gly Gly Lys Ser Gly Glu Leu Glu Gln Glu Glu Arg Leu Ser
                305                 310                 315
Lys Glu Trp Glu Asp Ser Lys Arg Trp Ser Lys Met Asp Gln Leu
                320                 325                 330
Ala Lys Glu Leu Thr Ala Glu Lys Arg Leu Glu Gly Gln Glu Glu
                335                 340                 345
Glu Glu Asp Asn Arg Asp Ser Ser Met Lys Leu Ser Phe Arg Ala
                350                 355                 360
Arg Ala Tyr Gly Phe Arg Gly Pro Gly Pro Gln Leu Arg Arg Gly
                365                 370                 375
Trp Arg Pro Ser Ser Arg Glu Asp Ser Leu Glu Ala Gly Leu Pro
                380                 385                 390
Leu Gln Val Arg Gly Tyr Pro Glu Glu Lys Lys Glu Glu Glu Gly
                395                 400                 405
Ser Ala Asn Arg Arg Pro Glu Asp Gln Glu Leu Glu Ser Leu Ser
                410                 415                 420
Ala Ile Glu Ala Glu Leu Glu Lys Val Ala His Gln Leu Gln Ala
                425                 430                 435
Leu Arg Arg Gly
```

HUMAN CHROMOGRANIN A (CGA) IMMUNOLOGIC ASSAY, ANTIBODIES, REAGENTS AND KITS FOR SAID ASSAY

DESCRIPTION

1. Technical Field

The subject of the present invention is a method for the immunoassay of human chromagranin A, with which it is possible in particular to assay not only chromogranin A in intact form, but also the major fragments of this chromogranin A.

Such assay may be used in particular for the diagnosis and follow-up of pathologies such as, for example, pheochromocytoma and intestinal carcinoids.

2. Prior Art

Chromogranin A (CgA) is a protein having a molecular weight of 48 kDa, a pI of 4.9, whose human form contains 439 amino acids as described by Konecki et al., 1987, in reference [1]. It belongs to the family of granins with which it shares structural and physiological similarities. CgA, like chromogranin B, shows marked inter-species preservation which presupposes a major function. CgA is largely represented in the secretagogues of endocrine and neuroendocrlne cells of which, along with the other granins, it forms one of the main components. It also acts at this level as a regulatory element of the cosecretion of other entities, such as the catecholamines in the adrenal gland.

CgA also plays an essential prohormone role via the release of active peptides, subsequent to intra-granular and extra-matricial proteolytic degradation.

Figure 1A:
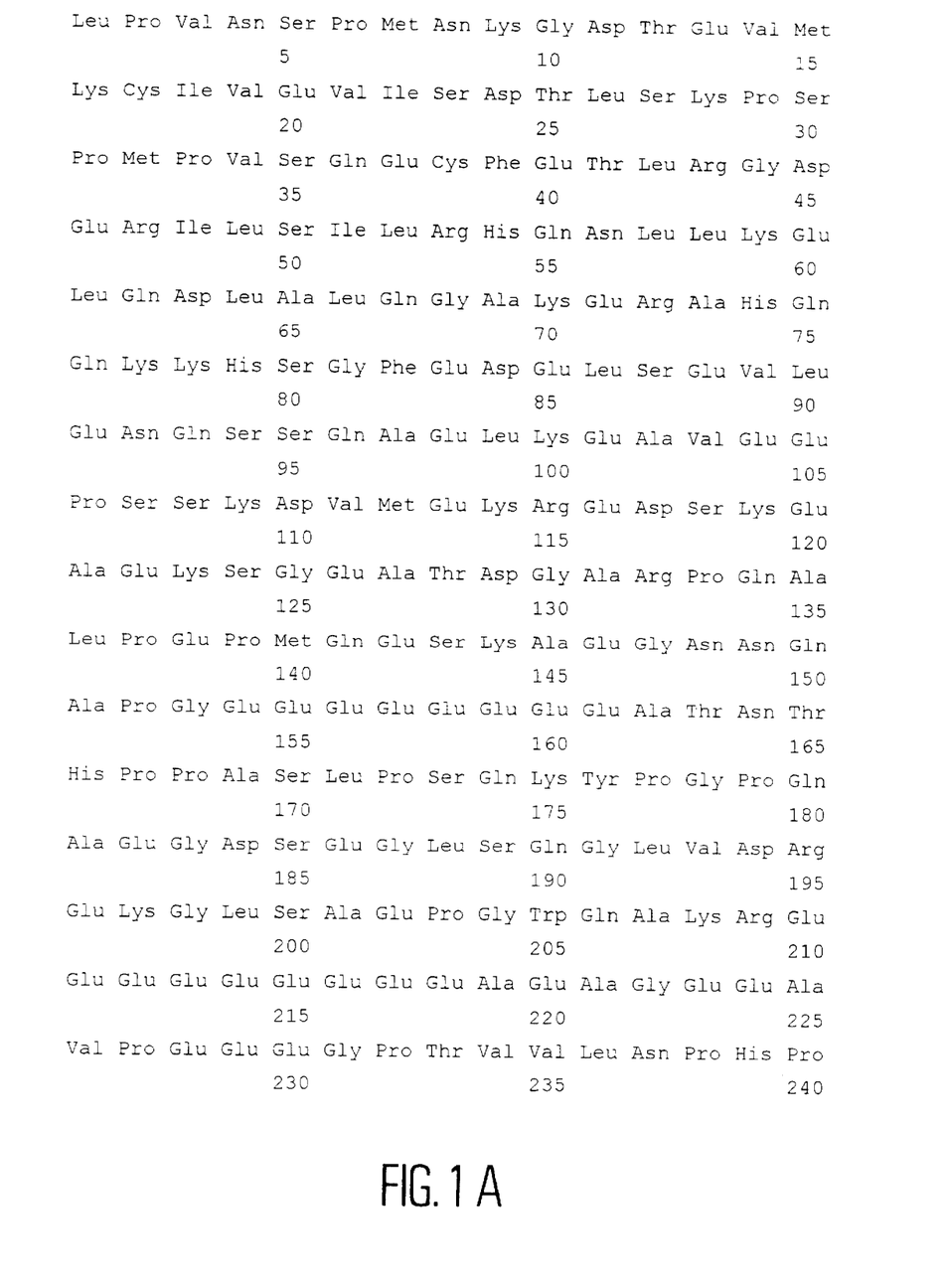
FIG. 1 illustrates SEQ ID NO:1 of the 439 amino acids of mature human CgA.
Figure 1B:
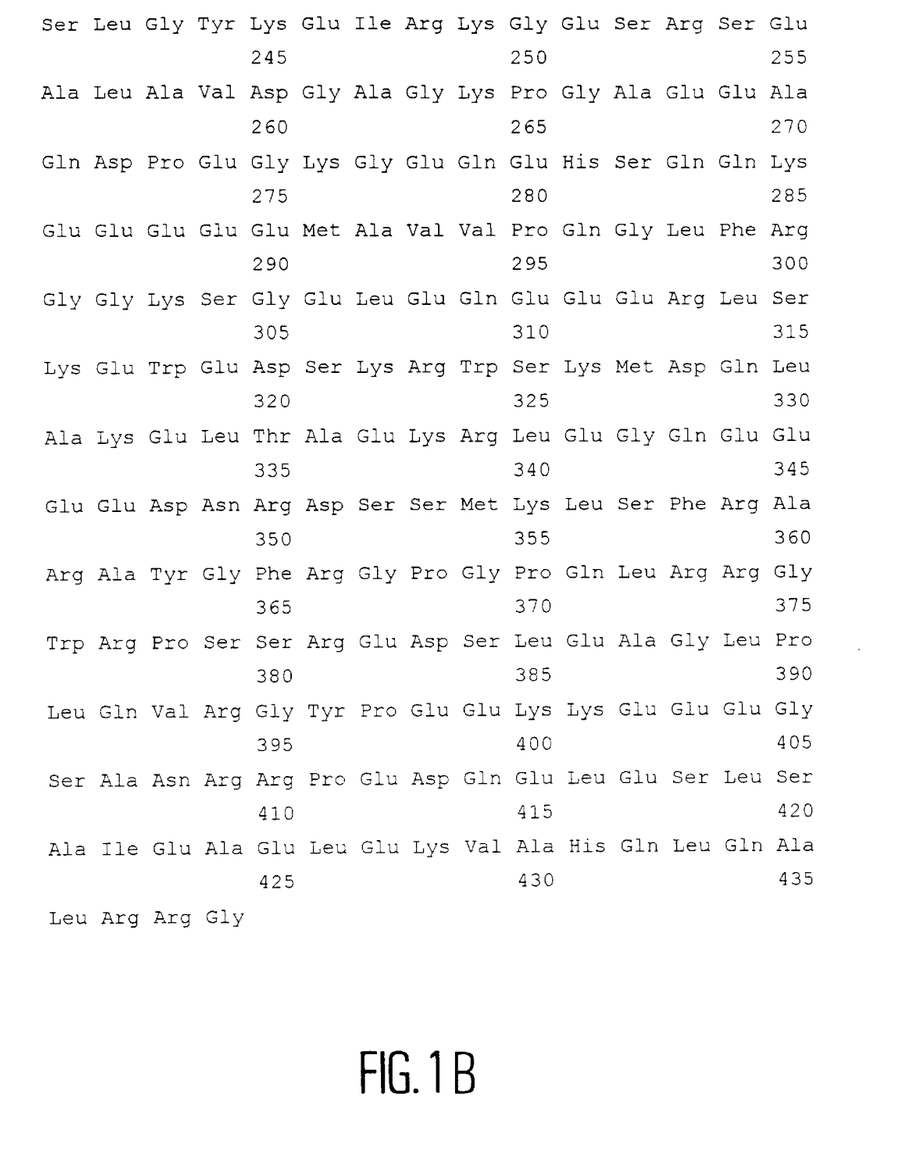

In appended FIG. 1, SEQ ID NO:1 is shown of the 439 amino acids described by Konecki et al., corresponding to human chromogranin-A.

Figure 2:
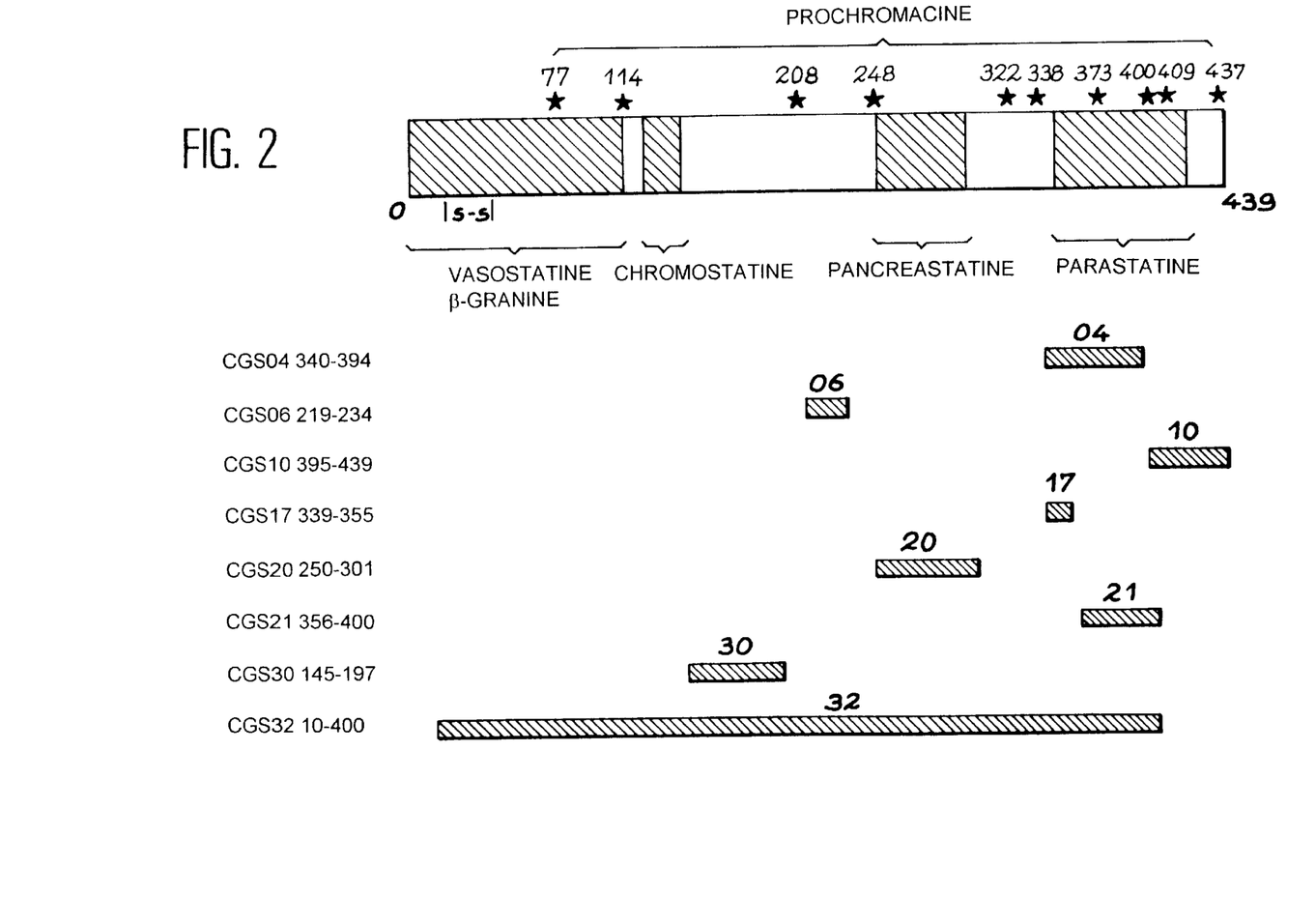
FIG. 2 illustrates, in simplified manner, the sequence of amino acids of human CgA with the fragments obtained by proteolysis and their positioning on this protein (SEQ ID NO:1). The asterisks and numbers associated therewith indicate the dibasic cleavage sites. The antibodies directed against some epitopes are listed below.

FIG. 2 shows this sequence in simplified fashion, identifying in this figure some of the peptides able to be released in man, i.e. the peptides: vasostatin/β granin, chromostatin, pancreastatin, parastatin and prochromacin. Protelysis affects the dibasic sites numbered and denoted by an asterisk in FIG. 2, which are distributed along the CgA sequence and total 10 in number in human CgA. This proteolysis has been described as a recurrent phenomenon either side of the protein ends, and it has been shown that it is specific to tissues and that it leads to substantial differences in the tissue distribution of the peptides produced. The degree of intensity and the type of proteolysis may therefore be responsible for the great variability of the fragments found in the tissues, blood circulation and urine.

Recent work by Corti et al., reference [2], has confirmed this diversity by showing that in patients suffering from pheochromocytoma there exist circulating forms of different conformation and in varying proportions from one person to another. In the same way, it has been shown, through research on the WE-14 peptide, that CgA is proteolysed in different manner in normal tissues and neoplasic tissues of the pancreatic gastro-enteral tract.

In addition to its detection in normal tissues and in corresponding neoplasias, numerous studies see a diagnostic advantage in the assay of CgA. The levels of circulating CgA are significantly high in cases of pheochromocytoma, carcinoid and endocrine pancreatic tumour. This data has been confirmed and extended to other pathologies: neuroblastoma, tumours of the gastro-intestinal tract, essential hypertension. The presence of CgA has been shown in a great number of neurodegenerative pathologies including Alzheimer's (see reference Munoz, Lab. Invest., 1991, vol. 64, pages 826–832 [15]). Some authors have also shown that the presence of CgA in cancers of the prostate could be the sign of an unfavourable development, as in the case of kidney cancer. The assay of Cga therefore offers a major advantage.

Document U.S. Pat. No. 4,758,522 [3] describes an immunoassay of CgA in which the CgA is measured by competitive assay with radiolabelled CgA for the sites of an anti-human CgA antibody.

Syversen et al. in reference [4], have described an assay of chromogranin A with the ELISA technique using an antibody directed against a C-terminal fragment of CgA corresponding to SEQ ID NO:1 amino acids 210 to 439 and radioimmunoassay of pancreastatin.

Corti et al., in reference [2], have also described two assays of CgA using monoclonal antibodies directed against SEQ ID NO:1 amino acids 81 to 90 and SEQ ID NO:1 amino acids 68 to 70 of human CgA.

These assays therefore take into consideration some CgA fragments, but they do not permit differentiation of pathological type on the results of the assay.

Indeed, proteolysis of the molecule and the multiplicity of the circulating fragments require an assay configuration which is able to detect the majority of these entities.

The purpose of the present invention is precisely a method of CgA immunoassay which measures the levels of intact CgA and the levels of major fragments found in circulating blood.

DISCLOSURE OF THE INVENTION

According to the invention, the immunoassay method for human chromogranin A (CgA) present in a sample comprises the use of at least one monoclonal or polyclonal antibody which binds specifically to an epitope positioned extending from (SEQ ID NO:1) amino acids 145 to 284 from the N-terminal end of human CgA.

According to the invention, the imunoassy method for human chromograinin A (CgA) present in a sample comprises the use of at least one monoclonal or polyclonal antibody which binds specifically to an epitope positioned extending from (SEQ ID NO:1) amino acids 145 to 284 from the N-terminal end of human CgA.

To implement this assay, to the sample to be assayed is added a quantity of labelled human CgA and the antibody which binds specifically to an epitope positioned in SEQ ID NO:1 amino acids 145 to 234 of CgA, and it is then left to incubate. In this manner, competitive conditions are set up between the sample CgA and the labelled CgA for the sites of this antibody. When the assay is conducted in heterogeneous phase, using a radioelement as label, it is possible to separate the antibody-hCgA complexes formed by immunoprecipitation using an appropriate antibody. By then determining the radioactivity of the complexes formed, it is possible to determine the CgA concentration of the sample with reference to a standard curve obtained from standard samples with known CgA concentrations.

It is also possible to conduct the assay in homogeneous phase, using labelled hCgA for example and an antibody able to modify the signal emitted by the labelled hCgA.

In this assay, advantageously the antibody used is specific to an epitope positioned in SEQ ID NO:1 amino acids 219 to 234 of human CgA, or the antibody specific to an epitope positioned in SEQ ID NO:1 amino acids 145 to 197 of human CgA. These antibodies are preferably monoclonal antibodies.

To carry out this assay, the preparation of the standard samples and labelled CgA may use purified human CgA from endocrine or neuroendocrine cells of human origin, or preferably recombinant human CgA.

According to a second embodiment of the invention, the immunoassay is a sandwich-type assay using a first monoclonal or polyclonal antibody which binds specifically to a first epitope positioned in SEQ ID NO:1 amino acids 145 to 234 of human CgA, and a second monoclonal or polyclonal antibody which binds specifically to a second epitope different from the first and also positioned in SEQ ID NO:1 amino acids 145 to 234 of human CgA, one of the two antibodies being labelled.

In this second embodiment of the invention, two antibodies are used that are specific to different epitopes, positioned in SEQ ID NO:1 amino acids 145 to 234 of CgA. This assay may be conducted in heterogeneous phase by immobilizing the first antibody on a solid phase and using a second, labelled antibody.

This assay may also be conducted in homogeneous phase, using a first labelled antibody and a second antibody able to modify the signal emitted by the first labelled antibody.

By way of example, the first antibody may be specific to an epitope positioned in the sequence of SEQ ID NO:1 amino acids 145 to 197 of CgA and the second antibody may be specific to an epitope positioned in SEQ ID NO:1 amino acids 219 to 234 of CgA.

It is also possible to use in this assay a first antibody specific to an epitope positioned in SEQ ID NO:1 amino acids 219 to 234 and a second antibody specific to an epitope positioned in SEQ ID NO:1 amino acids 145 to 197 of human CgA.

According to a third embodiment of the invention, the immunoassay is a sandwich-type assay using a first monoclonal or polyclonal antibody which binds specifically to an epitope positioned in SEQ ID NO:1 amino acids 145 to 234 of human CgA and a second monoclonal or polyclonal antibody which binds specifically to a second epitope positioned in SEQ ID NO:1 amino acids 250 to 301 of human CgA, one of the two antibodies being labelled.

In this embodiment of the invention, the assay may be conducted in heterogeneous phase using a first antibody immobilised on a solid phase and a second labelled antibody, or the reverse. It is also possible to carry out the assay in homogeneous phase, using a first labelled antibody and a second antibody able to modify the signal emitted by the first labelled antibody, or the reverse.

As first antibody, advantageously an antibody specific to SEQ ID NO:1 amino acids 145 to 194 of human CgA is used, or an antibody specific to SEQ ID NO:1 amino acids 219 to 234 of human CgA.

The method of the invention is particularly advantageous for the diagnosis and follow-up of pathologies such as pheochromocytoma or carcinoid tumours, as they permit positive discrimination between the sera from patients suffering from pheochromocytoma or carcinoid tumours and normal sera.

To implement the method of the invention, conventional immunoassay methods in heterogeneous phase can be used, which permit separation of the CgA-antibody complexes from the excess labelled antibody.

It is also possible, in the method of the invention, to use homogeneous phase assay methods which do not comprise such separation.

Homogeneous phase assay methods are based on the use of an antibody-antigen pair or a pair of two antibodies which, when they are close to one another, emit a different signal from the one they emit separately.

For this purpose, it is possible to use in particular an antibody coupled to a luminescent energy-acceptor compound and an antibody coupled to a luminescent energy-donor compound.

By way of example, the luminescent energy-acceptor compound may be allophycocyanine and the luminescent energy-donor compound may be a europium cryptate such as those described in EP-A-0 321 353 [II].

One homogeneous phase assay method of particular interest is the TRACE® method described in reference [4].

In respect of heterogeneous phase assays, a solid phase is used on which the non-labelled antibody used for the assay is immobilised.

The solid phases able to be used may be of different types. For example macroscopic solid phases may be used, formed of tubes, beads or fins in polymer or other materials.

The polymers able to be used are for example polystyrene, the polyamides, polypropylene, the polyoxymethylenes and styrene copolymers.

It is also possible to use finely divided microscopic solid phases, for example powders and aggregates in polymer, protein or other materials.

Under the invention, the term "labelled" applied to human CgA in the first embodiment of the invention or to the different antibodies in the second embodiment, shall mean that the CgA or the antibodies have been modified by a labelling element which may for example be a radioelement, a fluorescent element, a luminescent element, an enzyme, a fluorescent chromophore, a light-absorbing chromophore, or any other ligand permitting direct or indirect quantitative measurement.

The invention also concerns monoclonal antibodies specific to an epitope positioned either in SEQ ID NO:1 amino acids 145 to 197, or in SEQ ID NO:1 amino acids 219 to 234, of human chromogranin, and immunological reagents containing one of the antibodies bound to a detectable label or fixed onto a solid phase.

These antibodies are of particular interest since they are suitable for all types of assay. They give good results not only in assays conducted with conventional labels (radioelement, etc.) but also in assays conducted with fluorescent labels of cryptate and allophycocyanine type which generally can only be used with certain antibodies.

The invention also concerns immunoassay kits for human CgA containing the above-cited monoclonal. antibodies.

It also concerns an immunoassay kit for human CgA which contains:
a first antibody, and
a second antibody, at least one of the two antibodies being an antibody specific to an epitope positioned in SEQ ID NO:1 amino acids 145 to 234 of human CgA.

According to a first embodiment of the kit, the first antibody and the second antibody are chosen from among the antibodies specific to the epitopes positioned in SEQ ID NO:1 amino acids 145 to 197 and/or SEQ ID NO:1 amino acids 219 to 234 of human CgA.

According to a second embodiment of the kit, one of the antibodies is specific to an epitope positioned in SEQ ID NO:1 amino acids 145 to 197, or in SEQ ID NO:1 amino acids 219 to 234, and the other antibody is specific to an epitope positioned in SEQ ID NO:1 amino acids 250 to 301 of human CgA.

Preferably, when the kit is intended for a heterogeneous phase assay, one of the antibodies is immobilised on a solid phase and the other antibody is coupled to a detectable label.

The detectable label is iodine 125 for example.

Preferably, when the kit is intended for homogeneous phase assay, one of the antibodies is coupled to a luminescent energy-donor compound and the other antibody is coupled to a luminescent energy-acceptor compound.

Advantageously, the luminescent energy-donor compound is a europium cryptate and the luminescent energy-acceptor compound is allophycocyanine.

It also concerns a competitive immunoassay kit containing an antibody specific epitope positioned in SEQ ID NO:1 amino acids 145 to 234.

In this kit, the antibody is preferably specific to an epitope positioned in SEQ ID NO:1 amino acids 219 to 234 or in SEQ ID NO:1 amino acids 143 to 197 of human CgA.

According to the invention, the antibodies used for the assay may be polyclonal antibodies or monoclonal antibodies.

The polyclonal antibodies may be obtained from peptide fragments of human chromogranin A obtained by proteolysis of human CgA or by peptide synthesis, by in vivo or in vitro immunisation. In this case, it is necessary to couple the peptide fragment to a vector protein such as knee ligament hemocyanin (KLH) to obtain antibodies in animal.

The monoclonal antibodies may be obtained from hybridomas using the technique described by H. Kohler and C. Milstein described in Nature, 1975, 256, pages 495–497. In this case, one or more mice immunisations are made with whole chromogranin A or with peptide fragments corresponding to the desired epitopes, associated with a carrier protein, then the spleen of the animals is taken and cell fusion is made between the splenocytes and myeloma cells. The hybridomas produced are then screened to select the clones producing the antibodies specific to the epitopes of human CgA.

Preferably, according to the invention, monoclonal antibodies are used.

Other characteristics and advantages of the invention will be more clearly understood on reading the following description of examples of embodiment given evidently for illustrative, non-restrictive purposes with the reference to the appended drawings.

The following description illustrates the preparation of monoclonal antibodies directed against these different epitopes of human CgA, and the selection of antibodies suitable for the immunoassay of human chromogranin A.

1) Production of Monoclonal Antibodies

1. Isolation and Purification of Human CgA.

The method described by O'Connor et al. in reference [6] is used to purify hCgA from human adrenal glands of patients suffering from pheochromocytoma. The final separation of the protein is made by electrophoresis on 2-D gel using O'Farrel's original technique described in reference [7] and modified by Bader and Aunis as described in reference [8]. The CgA is electroeluted from gels. Recombinant human CgA is also produced (rhCgA) using an rhCgA-expressing strain of E. Coli BL21 (DE3) as described by Taupenot et al. in reference [9].

2.—Labelling of the Purified CgA ($^{125}$I-hCgA)

The native and recombinant CgAs are labelled with Na$^{125}$I using the chloramine T method of Hunter and Greenwood at a specific activity of 1500 kBq $\mu g^{-1}$. The free iodine is removed by filtration on Sephadex-G25 gel (Pharmacia Biotech). The fractions of radiolabelled protein are mixed and diluted in PBS, pH 7.2, containing 45 nmole/l NaN$_3$, 0.5% bovine serum albumin (BSA).

3.—Immunisations

Balb/c mice aged 6 to 8 weeks are respectively immunised by intraperitoneal route with 10 mg of purified hCgA or rhCga previously obtained in Freund's complete adjuvant. The following intraperitoneal doses in incomplete Freund's adjuvant at one month intervals. Follow-up of mice immunisations is made by serum titration through immunoprecipitation with $^{125}$I-hCgA previously obtained.

4—Production and Screening of Hybridomas

The mice are subsequently injected by intravenous route with 10 mg hCgA in a 0.9% NaCl solution three days before cell fusion. The spleen cells are isolated and are fused with P3-X63-Ag 8.653 myeloma cells in the presence of 37% polyethylene glycol (molecular weight 1540).

The positive clones are identified by immunoprecipitation with $^{125}$I-hCgA. The antibodies derived from positive clones are produced using mice ascites and are purified using sepharose-protein A gel.

Eleven fusions were made with mice immunised against hCgA. Only two were successful and generated 8 clones. The two fusions with animals immunised against recombinant hCgA protein produced 16 second-generation clones. Overall, 17 IgG1, 6 IgG2a and 1 IgG2b having levels varying from 2 to 3236 ng/ml were produced for characterization.

5—Identification of Monoclonal Antibodies

The different families of CgA epitopes were identified by testing the possible combinations of antibodies on Biacore® equipment following the manufacturer's instructions. All the antibodies tested were diluted in 50 mmol/l HEPES, 15 mmol/l EDTA, 0.75 M NaCl, pH 7.4 and injected in the proportion of 50 mg/ml. The same buffer was used for recombinant human CgA, diluted to 20 mg/ml.

This analysis on Biacore led to determining that the 24 antibodies tested are divided into eight epitope groups as shown in table 1. One of the groups (group 3) may nonetheless be subdivided on account of the partial inhibitions existing between the antibodies of this group.

The stoicheiometry of the immobilised antibody-rhCgA reaction varies from 0.157 to 0.621 antigen moles/antibody moles (see table 1).

The antibodies in each group or sub-group show a priori recognition of the same sequence.

6—Identification of Antibodies with the Peptides Derived from Recombinant Human CgA (rhCgA).

2 nmol of rhCgA are left to digest for 2 h at 37° C. with the Lys-C endoproteinase in a protein/proteinase ratio of 1000:1 in 100 nmole/l TRIS-HCL, pH 8.3.

The peptides derived from the rhCgA produced are then separated by HPLC on a Macherey gel column, NAGEL 300-5C18 (250 mm×4 mm). Absorbency is measured at 214 nm, and 0.1% trifluoroacetic acid in water is used as solvent system (solvent A) and 0.1% trifluoroacetic acid in acetonitirile (solvent B). The peptides are eluted at a rate of 0.7 ml/min using successive gradients of solvent B in solvent A from 0 to 25% for 10 minutes and from 25 to 75% for 50 minutes. Each peak fraction is collected and concentrated by evaporation but not to complete dryness.

Figure 3:
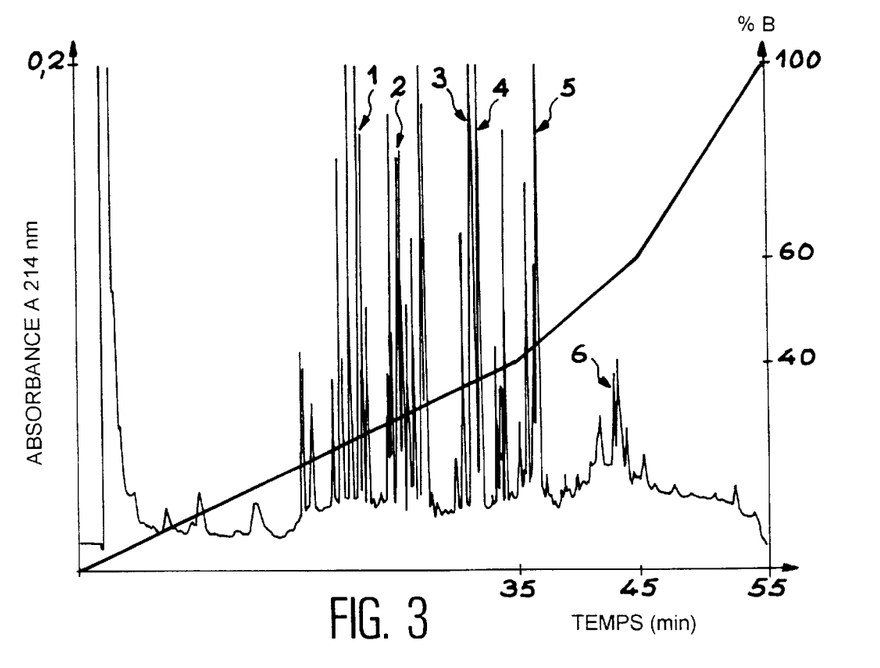
FIG. 3 shows the spectrum obtained during high performance liquid chromatography of recombinant human CgA after proteolysis with the endoprotease Lys-C.

FIG. 3 illustrates the fractions collected on leaving the column in relation to time, which are numbered 1 to 6.

The sequence of purified peptides is determined by Edman's automatic degradation on a 473 A microsequencer from Applied Biosystems. HPLC purified samples are loaded onto glass fibre filters pre-cycled and treated with polybrene. The amino-phenylthiohydantoine acids are identified by chromatography on a C-18 column (PTH C-18, 2.1 mm×200 mm). Analysis by mass spectrometry is carried out using the method described by Goumon et al. in reference [10].

These fractions are used to identify the monoclonal antibodies previously obtained. For this purpose, aliquot parts of the fractions are divided on nitrocellulose sheets. The membranes are quickly washed with NaCl/Pi (25 mM sodium phosphate, pH 7.5 containing 0.9% NaCl) and left to incubate for 2 hours at room temperature with the monoclonal antibodies diluted to $\frac{1}{1000}$ in NaCl/Pi.

The second antibody is an anti-mouse IgG conjugated with alkaline phosphatase. The enzyme reaction takes place in 100 mmol/l TRIS-HCL, pH 8:5, 100 mmol/l NaCl, 50 mmol/l MgCl$_2$ containing 0.4 mmol/l tetrazolium nitro-blue and 0.38 8mmol/l 5-bromo-4-chloro-3-indolyl phosphate.

A monoclonal antibody of each of the groups in table I is tested, i.e. antibodies CGS04, CGS06, CGS10, CGS30, CGS17, CGS21 and CGS32 previously produced, against each aliquot fraction of the rhCgA fragments separated by high performance liquid chromatography.

Table 2 illustrates the correlation between the different fractions and the antibodies recognizing these fractions. Table 2 also gives the mass of fragments isolated in each fraction, their position from the N-terminal end of chromogranin A and their N-terminal sequence. The antibodies CGS17 and CGS21 recognize the C-terminal domain of the protein with high specificity for SEQ ID NO:1 amino acids 339 to 355 and 356 to 400. The antibodies CGS04 and CGS10 are directly tested by Western-blot and the immuno-detected fragments are positioned in the C-terminal region of CgA(SEQ ID NO:1 amino acids 340 to 394 and 395 to 439).

Antibodies CGS06, CGS20 and CGS30 are specific to SEQ ID NO:1 amino acids 145 to 234 of the protein and correspond to SEQ ID NO:1 fragments of amino acids 198 to 245, 246 to 303, and 145 to 197, respectively. Finally, it is noticed that the antibody CGS32 is strongly reactive with a major fragment which extends from SEQ ID NO:1 amino acids 10 to 400. Having regard to the behavior of this antibody in association with other antibodies recognizing various CgA regions, it appears to recognize more specifically SEQ ID NO:1 amino acids 145 to 234.

In parallel, the sequence of the epitope of antibody CGS06 was specified by synthetic peptides. SEQ ID NO:1 amino acids 198 to 245 shows a high proportion of glutamic acids, a region that is particularly hydrophilic and potentially immunogenic. In particular it contains a first zone of 9 contiguous glutamic acids (SEQ ID NO:1 amino acids 210 to 218), and more especially a sequence of 3 glutamic aids flanked by two prolines (SEQ ID NO:1 amino acids 227 to 232). Two peptides, biotinylated at N-terminal position, corresponding to SEQ ID NO:207 to 234 and 219 to 245, were synthesized. These peptides were immobilised on tubes previously coated with streptavidin. The radiolabelled antibodies CGS30, CGS06 and CGS20 (2 kBq per ml) were incubated for 4 hours at room temperature under shaking with each of the peptides. The tubes were then washed and counted. The two antibodies CHS20 and CGS30 do not recognize either of the two peptides. On the other hand, CGS06 shows significant fixation on both sequences. The minimum deducted sequence therefore corresponds to SEQ ID NO:1 amino acids 219 to 234, a zone which encompasses the poly-Glu (SEQ ID NO:1 amino acids 227 to 232) site mentioned above.

In the same manner, the epitope of CGS20 was specified in relation to the sequence of pancreastatin. In this case, a synthetic peptide corresponding to pancreastatin(SEQ ID NO:1 amino acids 250 to 301 of human CgA) was added in increasing quantities in the second incubation of the following immunoradiometric assays: CGS06/CGS30* and CGS06/CGS20*. In the former case no inhibition of the signal was visible, providing evidence that neither CGS06 nor CGS30 recognize SEQ ID NO:1 amino acids 250 to 301. For the CGS06/CGS20* system on the other hand, a growing inhibition is obtained if the quantities of added peptide are increased (86% inhibition for 0.5 μg peptide per tube). CGS20 therefore does well recognize SEQ ID NO:1 amino acids 250 to 301 of human CgA, a sequence corresponding to pancreastatin.

FIG. 2 shows the position of these antibodies in relation to the whole molecule of chromogranin A and also indicates the sequences recognized by these antibodies.

According to the invention, it was found that the antibodies CGS06, CGS20 and CGS30 (or CGS33) made it possible to conduct specific immunoassays that are reproducible and precise. The antibodies CGS30 (or CGS33) may be used for competitive immunoassay.

The antibodies CGS06, CGS20 and CGS30 (or CGS33) may be coupled in pairs to conduct a sandwich-type assay.

The following examples illustrate assays of this type.

EXAMPLE 1

Radioimmunoassay of Human Chromogranin A.

In this example, the antibody used for the assay is CGS06 which is specific to SEQ ID NO:1 amino acids 219 to 234 of chromogranin A. To conduct this assay, standard samples of recombinant human chromogranin (rhCgA) are prepared, diluted in normal human serum. The rhCgA concentrations of the standard samples range from 0 up to 1600 ng/ml.

Also iodine 125-labelled rhCgA is used as described previously.

To conduct this assay, to a 50 ml tube of standard sample or sample to be assayed is added 300 μl hCgA, radiolabelled to the proportion of 2 kBq per tube, and 150 ml of the solution of CGS06 antibody purified to 80 ng/ml. A first incubation is carried out for 24 hours at room temperature under mild shaking. The bound complexes are then separated for 20 minutes at room temperature by adding 75 µl sheep anti-mouse immunoglobulins diluted to $1/10^{th}$ in PBS and 50 ml normal human serum. 1 ml of 6% polyethylene glycol is added (molecular weight 6000) and the precipitated complexes are separated by centrifuging at 2000 g for 15 minutes. Their radioactivity is then determined in a gamma counter.

From the standard samples a standard curve is obtained, and the chromogranin A concentration of the sample to be assayed is determined by locating the value found on this standard curve.

The detection limit determined by measurement repeatability at standard 0 (Bmax-2σ per n=10 measurements) was calculated at 14 ng/mL. The assay at 10 points of 2 sera having a concentration of 243 and 450 ng/mL made it possible to evaluate an intra-assay precision of 0.9% on the two samples. In parallel, the inter-assay precision test made by the assay on these same sera in 3 different experiments shows a VC of 4.5 and 6.4% respectively.

This assay was tested on a series of 46 EDTA plasmas taken from healthy persons, and on 211 other plasmas from patients suffering from neuroendocrine or other pathology.

Figure 4:
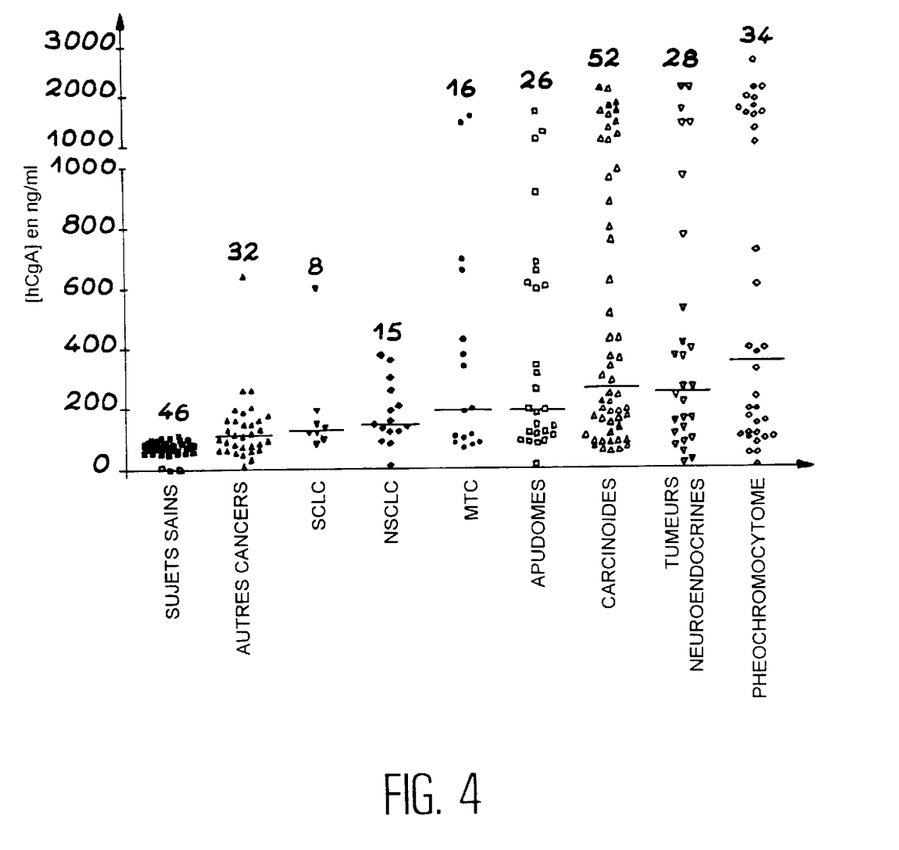
FIG. 4 is a diagram showing the distribution of the different populations tested by competitive assay (RIA) according to the invention. The number of cases tested is given above each assay group. The lines indicate the median for each assay group.

FIG. 4 shows the results obtained with this assay on the different plasmas tested. In this figure the nature of the pathologies is shown and the number of cases in each group of patients.

Variance analysis comparing pairs of normal population and each of the other populations shows that in each case the CgA levels are significantly higher in the pathological plasmas (p<0.0001). On the other hand, when the different groups of plasmas are compared with the series of plasmas from non-neuroendocrine cancers, analysis shows that the groups concerning small cell lung cancers (SCLC) or non-small cell lung cancers (NSCLC) are not significantly different from the reference population (p=0.2863 and 0.1798 respectively). The other groups studied show CgA values that are significantly greater in particular in respect of carcinoids and pheochromocytomas (p<0.0001) as well as APUDomas and other neuroendocrine tumours (p<0.001).

In this assay, the CgA levels found were the following:

40 ng/ml for the pool (NP) of plasmas from healthy individuals, 675 nm/ml for the pool (PP) of plasmas from persons suffering from pheochromocytoma, and 1600 ng/ml for the pool (CP) of plasmas from persons suffering from intestinal carcinoid tumours.

EXAMPLE 2

Assay of Chromogranin A Using a Sandwich Method (IRMA Method).

For this assay, two different antibodies are used, the first antibody is the antibody CGS06 specific to SEQ ID NO:1 amino acids 219 to 234, and the second antibody is the CGS30 antibody specific to SEQ ID NO:1 amino acids 145 to 197. The first antibody is brought to a concentration of 10 µg/ml in PBS, pH 7.5, and polystyrene tubes are coated with this antibody.

The second antibody CGS30 is labelled with iodine 125 with $Na^{125}I$ using the chloramine T method, previously described for the labelling of rhCgA, at a specific activity of 400 kBq/µg. The standards are the same as those previously described in example 1.

The buffer used for the assay is made of 50 mmol/l $Na_2HPO_4/KH_2PO_4$, 1 mmol/l EDTA, 15 mmol/l $NaN_3$, 1% BSA, pH 7.0.

For each assay, 1 ml of assay buffer and 50 µl of standard sample or sample to be assayed are added to the tubes coated with the CGS06 antibody. They are left to incubate for 18 hours at room temperature. The tubes are then washed twice with 2 ml of 0.3% Tween 20 solution. 1 ml of the labelled CGS30 antibody is then added to each tube and they are left to incubate for 2 hours at room temperature under gentle shaking. The tubes are again washed as previously described and their radioactivity is determined on a gamma counter.

As in example 1, a calibration curve is obtained from the standard samples of known concentrations, and the chromogranin A concentration of the sample to be assayed is determined with reference to the standard curve.

To check the specificity of the assay, it is conducted on a normal pool (NP) and on two pathological pools obtained from EDTA taken respectively from patients suffering from pheochromocytoma (PP) or intestinal carcinoids (CP).

This specificity is assessed by determining the ratio of CgA concentrations between the pathological pool PP or CP and the normal pool NP.

In the case of this example, the CgA concentration ratios PP/NP and CP/NP are as follows:

PP/NP=9.9

CP/NP=18.2

For the assay of example 1, the ratios were the following:

PP/NP=16.9

CP/NP=40

By way of comparison, the binding percentage obtained for the standard sample at 1200 ng/ml is 65.51.

This combination of antibodies therefore permits a high signal to be obtained and to differentiate between the two pathological pools.

In table 3, appended, the results are given which were obtained by conducting the same sandwich assay with different pairs of antibodies.

These results show that the two antibodies CGS06 and CGS30 associated together or with the antibody CGS20 give a satisfactory signal and make it possible to discriminate between the two pathological pools.

By way of comparison, the same assay was conducted using other antibodies in table 2, but these did not yield satisfactory results.

Therefore, if CGS21 or CGS10 is used as the second labelled antibody, it is impossible to discriminate between the pathological pool PP and the pool NP, since the PP/NP ratio is not greater than 2, and is even less than 1.

Other combinations such as CGS21/CGS06*, CGS21/CGS30* or CGS32/CGS06* are not of interest since they do not allow differentiation between the two pathological pools, the ratios PP/NP and CP/NP being close.

Figure 5:
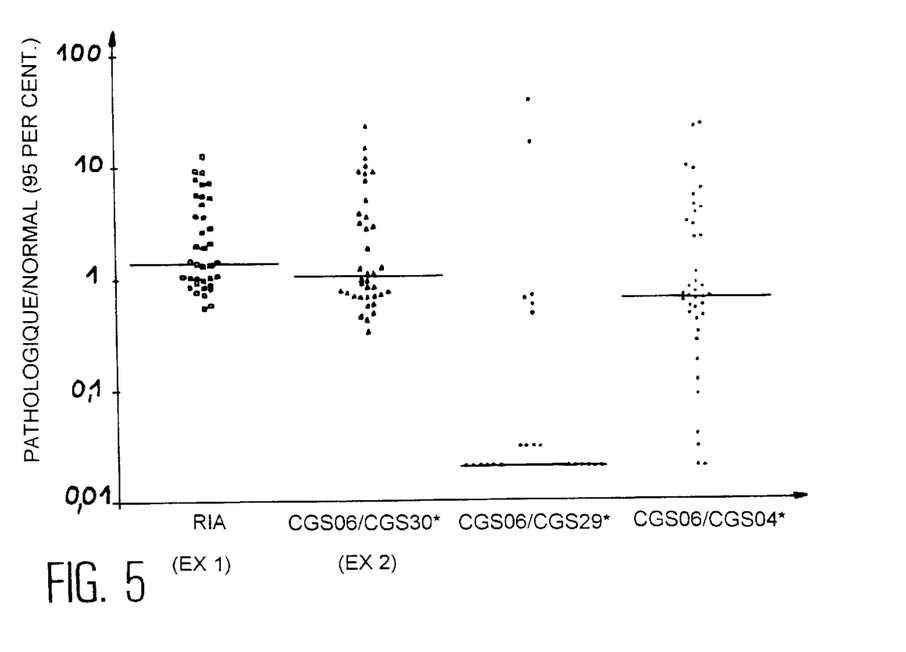
FIG. 5 is a diagram illustrating the results obtained with three sandwich-type assays compared with the competitive assay using different antibodies. The results are expressed in the form of a ratio of pathological plasma concentrations over the value of the 95$^{th}$ percentile of a normal population (n=20). The lines indicate the median for each assay group.

FIG. 5 gives the results of the immunoassays of examples 1 and 2 according to the invention and of two other assays using the sandwich method as in example 2, but with the combination of antibody CGS06/labelled CGS29*. and the combination CGS06/labelled CGS04*. The two antibodies CGS29 and CGS04 recognize the C-terminal part of CgA. The antibody CGS29 shares the same epitope with CGS10.

In this figure, the results are expressed in the form of the ratio between the concentration of pathological plasma and the value of the $_{95}$th percentile of the normal population (n=20). The straight lines indicate the median for each group.

This figure shows that equivalent results are obtained with examples 1 and 2. On the other hand, with the pair CGS06/CGS04* the correlation deteriorates and a certain number of samples have a considerably lowered CgA level. In the assay with CGS06/CGS29*, the phenomenon is further amplified, with a very marked decrease in measured concentrations, the CgA level being undetectable in 50% of the population.

Therefore, the best results are obtained with the antibodies of SEQ ID NO:1 acids 145 to 234 of CgA, in accordance with the invention.

EXAMPLE 3

Assay of Chromogranin A Using a Homogeneous Phase Sandwich Method, and Using Fluorescence (FIA Method).

For this assay, two different antibodies are used, the first antibody is the antibody CGS06 specific to SEQ ID NO:1 amino acids 219 to 234 and the second antibody is the CGS30 antibody (or CGS33) specific to SEQ ID NO:1 amino acids 145 to 197. The first antibody CGS06 was conjugated with europium cryptate which is an energy-donor compound.

The second antibody CGS30 (or CGS33) was conjugated with allophycocyanine which is an energy-acceptor compound.

The europium cryptate used is the cryptate Eu trisbipyridine diamine (TBP ($Eu^{2+}$) cryptate). It is described in document EP-A-321 353 [II] and meets the formula:

The CGS06-cryptate conjugate is prepared using the method described by Lopez et al. in Clin. Chem., 39, 1993, pages 196–201 [12].

The CGS30 (or CGS33)-allophycocyanine (APC) conjugate is prepared using the method described in WO92/01225 [13]. For the assay, the following buffers are used:

conjugate buffer: 50 mM $PO_4$ pH 7.0, 0.1% BSA, 1.5 mM EDTA, 1.5 MM normal mouse immunoglobulins, 600 mM KF, 0.1% Kathon, incubation buffer: 50 mM $PO_4$ pH 7.0, 1% BSA, 1.5 mM EDTA, 10% normal human serum, 0.1% Kathon.

To each well of a black, 96-well multidish and in the following order is added:

100 µl CGS06-cryptate conjugate diluted in the conjugate buffer, at a concentration of 0.5 g/ml, 100 µl CGS30 (or CGS33)-APC conjugate diluted in the conjugate buffer, at a concentration of 5 pg/ml, and 100 µl of calibrator or sample to be assayed diluted in the incubation buffer.

They are left to incubate for 1 hour at 37° C., then the fluorescence of each well is measured at 620 and 665 nm on dedicated equipment, as described by Mathis in Clin. Chem. 39, 1993, pages 1953–1959 [14].

Figure 6:
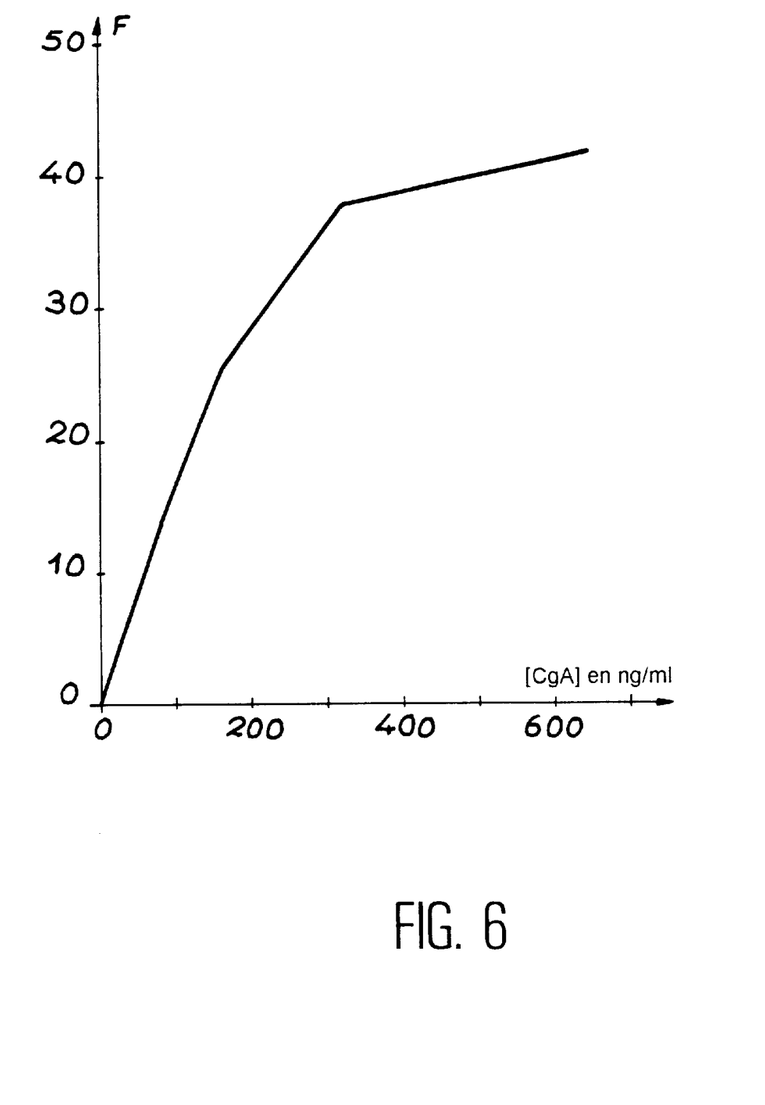
FIG. 6 shows the curve obtained, that is to say the human CgA concentration of a sample (in ng/ml) in relation to detected fluorescence (F), using a homogeneous phase assay according to the invention.

The results obtained are given in FIG. 6 which shows the CgA concentration (in ng/ml) in relation to the detected signal.

The sensitivity of the assay thus conducted with the antibodies CGS06 and CGS30 (or CGS33) is 1.5 ng/ml, and the intra-assay variation coefficients are 2.88% for a CgA concentration of 15.7 ng/ml, 1.5% for a concentration of 50 ng/ml, and less than 1% for any concentration above 50 ng/ml. The inter-assay variation coefficients are 1.2% for a CgA concentration of 70 ng/ml (n=11 assays), 1.7% for a concentration of 409 ng/ml (n=10).

A recovery test is conducted by overloading pathological serum samples A to H having a known CgA concentration with a determined quantity of purified recombinant human CgA free of contaminant fragments. The rate of recovery is calculated by determining the ratio between the human CgA concentration measured with this assay and the theoretical concentration of the mixture. The results of this test are given in table 4. The levels of recovery obtained lie between 93.4% and 106%, which indicates that the antibodies chosen for this assay allow recognition identity between the human CgA contained in pathological samples and the purified recombinant human CgA free of contaminant fragments.

Figure 7:
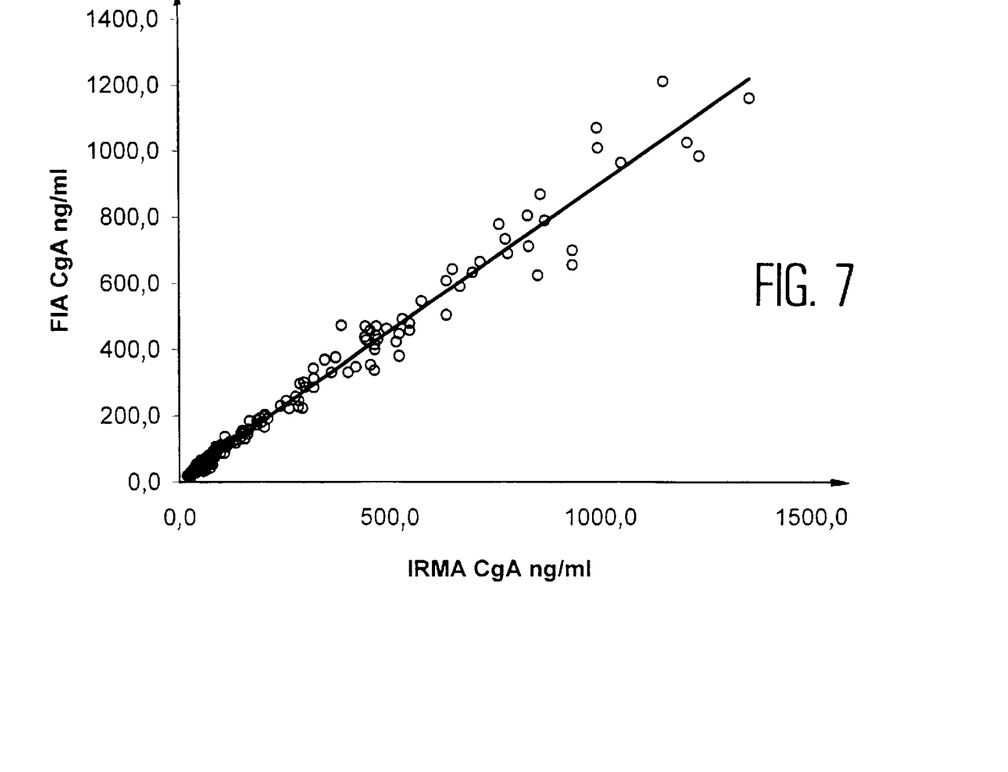
FIG. 7 is a diagram illustrating the correlation between the results obtained with FIA and IRMA assays of CgA (in ng/ml).

A correlation was made between the IRMA assay described in example 2 (CGS06 and CGS30) and the FIA assay of example 3 using the antibodies CGS06 and CGS33, on 100 normal samples and 95 samples from patients suffering from a tumour pathology of neuroendocrine type. The results are given in FIG. 7. The equation of the straight line obtained corresponds to y=0.8964x=7.4205 and the coefficient of determination obtained is 0.9776.

Figure 8:
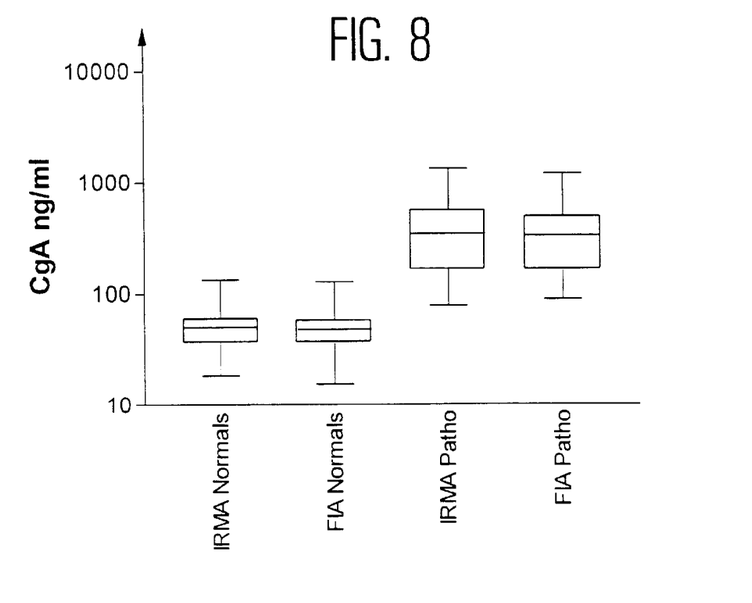
FIG. 8 shows the CgA levels (in ng/ml) obtained with normal samples and pathological samples using the IRMA and FIA assays of FIGS. 2 and 3.

The comparative study of the 100 normal samples and 95 pathological samples, whose results are given in FIG. 8 and table 5, shows good discrimination between these two types of samples, and extensive agreement between the FIA assay (CGS06/CGS33) described in example 3 and the IRMA assay (CGS06/CGS30) of example 2. This agreement confirms the importance of using an antibody directed against SEQ ID NO:1 amino acids 145 to 197 in association with CGS06 directed against SEQ ID NO:1 amino acids 219 to 234.

Cited References

[1]: Konecki et al., Biol. Chem., 262, 1987, pages 17026–17030.
[2]: Corti et al., Br. J. Cancer, 73, 1996, pages 924–932.
[3]: U.S. Pat. No. 4,758,522.
[4]: Syversen et al., Acta Oncologica, 32, n°2, 1993, pages 161–165.
[5]: Kohler & Milstein, Nature, 1975, 256, pages 495–497.

[6]: O'Connor et al., New Engl. J. Med., 1984, 311, pages 764–770.
[7]: O'Farrel, J. Biol. Chem., 72, 1975, pages 248–254.
[8]: Bader & Aunis, Neuroscience, 8, 1983, pages 165–181.
[9]: Taupenot et al., Regul Pept., 56, 1995, pages 71–88.
[10]: Goumon et al., Eur. J. Biochem., 235, pages 516–525.
[11]: EP-A-0 321 353.
[12]: Lopez et al., Clin. Chem., 39, 1993, pages 196–201.
[13]: WO 92/01225.
[14]: Mathis, Clin. Chem., 39, 1993, pages 1953–1959.
[15]: Munoz, Lab. Invest., 1991, vol. 64, pages 826–832.

TABLE I

| Antibody | Isotype | Stoicheiometry | Epitope group |
|---|---|---|---|
| CGS01 | IgG1 | 0.431 | 1 |
| CGS03 | IgG1 | n.t. | |
| CGS04 | IgG2b | 0.365 | |
| CGS12 | IgG1 | 0.364 | |
| CGS06 | IgG2a | 0.503 | 2 |
| CGS08 | IgG1 | 0.457 | |
| CGS10 | IgG1 | 0.182 | 3a |
| CGS05 | IgG1 | 0.157 | |
| CGS23 | IgG2a | 0.604 | |
| CGS24 | IgG2a | 0.521 | |
| CGS25 | IgG2a | 0.553 | |
| CGS26 | IgG2a | 0.356 | |
| CGS29 | IgG1 | 0.621 | 3b |
| CG534 | IgG1 | 0.536 | |
| CG535 | IgG1 | 0.539 | 3c |
| CGS30 | IgG2a | 0.327 | 4 |
| CGS31 | IgG1 | 0.198 | |
| CG533 | IgG1 | 0.383 | |
| CG536 | IgG1 | 0.184 | |
| CGS17 | IgG1 | 0.162 | 5 |
| CGS19 | IgG1 | 0.361 | |
| CGS20 | IgG1 | 0.254 | 6 |
| CGS21 | IgG1 | 0.183 | 7 |
| CGS32 | IgG1 | 0.262 | 8 |

| Fraction | Antibody | N-terminal sequence | Mass (Da) | SEQ ID NO: 1 amino acids |
|---|---|---|---|---|
| 1 | CGS17 | Arg Leu Glu Gly Gln Glu Glu | 2305.9 | 339–355 |
| 2 | CGS30 | Ala Glu Gly Asn Asn Gln Ala | 5635.8 | 145–197 |
| 3 | CGS20 | Gly Ile Arg Lys Gly Glu Ser Arg Ser | 6224.8 | 246–303[3] |
| 4 | CGS06 | Gly Le Ser Ala Glu Pro Gly | 5265.4 | 198–245[2] |
| 5 | CGS21 | Le Xaa[1] Phe Arg Ala Arg Ala | 5145.8 | 356–400 |
| 6 | CGS32 | Gly Xaa[1] Thr Glu Val Met Lys Xaa[1] Ile Val | 43532 | 10–400 |
| * | CGS04 | Leu Glu Gly Gln Glu Glu | n.d. | 340–394 |
| * | CGS10 | Gly Tyr Pro Glu Glu Lys | n.d. | 395–439 |

[1] Xaa = undetermined amino acid
[2] The sequence was specified using synthetic peptides. It could be shown that the recognized sequence is in fact restricted to SEQ ID NO: 1 amino acids 219 to 234.
[3] Also, it was possible that the antibody CGS20 recognizes a more restrictive epitope corresponding to SEQ ID NO: 1 amino acids 250 to 301 (human pancreastin).

TABLE 3

| Antibody combination | | Percentage bonding with standard 1200 ng/ml | CgA concentration ratio | |
|---|---|---|---|---|
| 1st antibody on solid phase | 2nd antibody labelled with $^{125}I$ | | PP/NP | CP/NP |
| CGS06 | CGS30* | 65.51 | 9.9 | 18.2 |
| CGS30 | CGS06* | 57.56 | 16.0 | 25.0 |
| CGS06 | CGS20* | 12.8 | 4.0 | 23.2 |
| CGS20 | CGS06* | 25.43 | 2.0 | 15.6 |
| CGS30 | CGS20* | 22.04 | 5.6 | 21.8 |
| CGS20 | CGS30* | 43.22 | 2.6 | 12.8 |

TABLE 4

| Sera | Recombinant human CgA added (ng/ml) | CgA assayed (ng/ml) | Theoretical CgA concentration (ng/ml) | % recovery |
|---|---|---|---|---|
| A | 0 | 61.3 | 61.3 | 100.0% |
| | 50 | 109.3 | 111.3 | 98.2% |
| | 200 | 250.9 | 261.3 | 96.0% |
| | 400 | 438.9 | 461.3 | 95.1% |
| B | 0 | 183.9 | 183.9 | 100.0% |
| | 50 | 243.6 | 233.9 | 104.1% |
| | 200 | 397.5 | 383.9 | 103.5% |
| | 400 | 610.5 | 583.9 | 104.6% |
| C | 0 | 118.7 | 118.7 | 100.0% |
| | 50 | 172.7 | 168.7 | 102.4% |
| | 200 | 328.4 | 318.7 | 103.0% |
| | 400 | 538 | 518.7 | 103.7% |
| D | 0 | 528 | 528 | 100.0% |
| | 50 | 584.6 | 578 | 101.1% |
| | 200 | 719.8 | 728 | 98.9% |
| | 400 | 889.3 | 928 | 95.8% |
| E | 0 | 40.1 | 40.1 | 100.0% |
| | 50 | 90.3 | 90.1 | 100.2% |
| | 200 | 228.6 | 240.1 | 95.2% |
| | 400 | 410.9 | 440.1 | 93.4% |
| F | 0 | 45.7 | 45.7 | 100.0% |
| | 50 | 100.1 | 95.7 | 104.6% |
| | 200 | 260.5 | 245.7 | 106.0% |
| | 400 | 467.3 | 445.7 | 104.8% |
| G | 0 | 187.7 | 187.7 | 100.0% |
| | 50 | 235.5 | 237.7 | 99.1% |
| | 200 | 379.9 | 387.7 | 98.0% |
| | 400 | 561 | 587.7 | 95.5% |
| H | 0 | 206.7 | 206.7 | 100.0% |
| | 50 | 263.5 | 256.7 | 102.6% |
| | 200 | 419.1 | 406.7 | 103.0% |
| | 400 | 614.9 | 606.7 | 101.4% |

TABLE 5

| X labels | IRMA Normal | FIA Normal | IRMA Patho. | FIA Patho. |
|---|---|---|---|---|
| N° of values | 100 | 100 | 95 | 95 |
| Minimum | 19 | 16 | 160 | 90 |
| 25% Percentile | 37 | 37 | 170 | 160 |
| Median | 50 | 48 | 350 | 330 |
| 75% Percentile | 61 | 59 | 560 | 500 |
| Maximum | 130 | 130 | 1400 | 1200 |

What is claimed is:

1. A method for measuring human chromogranin A (CgA) in a sample, comprising contacting the sample with at least one antibody which binds specifically to an epitope positioned in amino acids 145 to 197 of SEQ ID NO:1 and measure the CgA in the sample.

2. The method according to claim 1, which is a competitive immunoassay between the chromogranin A of the sample and a given quantity of labeled chromogranin A, for the sites of said antibody.

3. The method according to claim 1, wherein the chromogranin A is labeled with a label selected from the group consisting of radioisotopes, luminescent elements, enzymes, fluorescent chromophores, and light-absorbing chromophores.

4. The method according to claim 1, which comprises contacting the sample with a first antibody which binds specifically to a first epitope of human CgA, and a second antibody which binds specifically to a second epitope of human CgA different from the first, wherein at least one the epitopes being positioned in amino acids 145 to 197 of SEQ ID NO:1 and wherein one of the two antibodies is labeled.

5. The method according to claim 4, wherein the first and the second antibody are specific to an epitope positioned in amino acids 145 to 197 of SEQ ID NO:1.

6. The method according to claim 4, wherein the first antibody is specific to an epitope positioned in amino acids 145 to 197 of SEQ ID NO:1 and the second antibody is specific to an epitope positioned in amino acids 219 to 234 of SEQ ID NO:1 or amino acids 250 to 301 of SEQ ID NO:1.

7. The method according to claim 4, wherein the labeled antibody is labeled with a label selected from the group consisting of radioisotopes, luminescent elements, enzymes, fluorescent chromophores, and light-absorbing chromophores.

8. The method according to claim 4, wherein one of said antibodies is labeled with an energy-donor luminescent compound, and the other of said first and second antibodies is coupled to an energy-acceptor luminescent compound.

9. The method according to claim 8, wherein the energy-donor luminescent compound is a europium cryptate and the energy-acceptor luminescent compound is allophycocyanine.

10. A monoclonal antibody able to bind itself which binds specifically to an epitope positioned in amino acids 145 to 197 of SEQ ID NO:1.

11. An immunological reagent comprising the monoclonal antibody of claim 10 coupled to a detectable label selected from the group consisting of radioisotopes, energy-donor luminescent compounds, and energy-acceptor luminescent compounds.

12. A kit comprising:
   a first antibody, and
   a second antibody wherein at least one of the first and second antibodies being specific to an epitope positioned in amino acids 145 to 197 of SEQ ID NO:1.

13. The kit according to claim 12, wherein the first antibody and the second antibody are specific to an epitope positioned in amino acids 145 to 197 of SEQ ID NO:1.

14. The kit according to claim 12, wherein one of the antibodies is specific to an epitope positioned in amino acids 145 to 197 of SEQ ID NO:1, and the second antibody is specific to an epitope positioned in amino acids 250 to 301 of SEQ ID NO:1.

15. The kit according to claim 12, wherein one of the first and second antibodies is labeled with an energy-donor luminescent compound and the other of said first and second antibodies is coupled to an energy-acceptor luminescent compound.

16. The kit according to claim 15, wherein the energy-donor luminescent compound is a europium cryptate and the energy-acceptor luminescent compound is allophycocyanine.

17. An immunoassay kit comprising an antibody specific to an epitope positioned in amino acids 145 to 234 of SEQ ID NO:1.

18. The method according to claim 1, wherein the contacting is conducted in a homogeneous phase.

19. The method according to claim 1, wherein the sample contacting is conducted in a heterogeneous phase.

20. The method according to claim 2, wherein the antibody is a monoclonal antibody.

21. The method according to claim 4, wherein the first and second antibodies are monoclonal antibodies.

* * * * *

UNITED STATES PATENT AND TRADEMARK OFFICE
CERTIFICATE OF CORRECTION

PATENT NO. : 6,632,624 B1
DATED : October 14, 2003
INVENTOR(S) : Degorce et al.

It is certified that error appears in the above-identified patent and that said Letters Patent is hereby corrected as shown below:

<u>Title page,</u>
Item [86], should read:
-- [86]  PCT No.:  PCT/FR99/01141

§ 371 (c)(1),
      (2), (4) Date:  Nov. 14, 2000 --

Signed and Sealed this

Twentieth Day of January, 2004

JON W. DUDAS
*Acting Director of the United States Patent and Trademark Office*

SEQUENCE LISTING

<160> NUMBER OF SEQ ID NOS: 1

<210> SEQ ID NO 1
<211> LENGTH: 439
<212> TYPE: PRT
<213> ORGANISM: Homo sapiens
<220> FEATURE:
<221> NAME/KEY: DOMAIN
<222> LOCATION: (145)..(234)
<223> OTHER INFORMATION:
<221> NAME/KEY: DOMAIN
<222> LOCATION: (219)..(234)
<223> OTHER INFORMATION:
<221> NAME/KEY: DOMAIN
<222> LOCATION: (145)..(197)
<223> OTHER INFORMATION:
<221> NAME/KEY: DOMAIN
<222> LOCATION: (250)..(301)
<223> OTHER INFORMATION:
<221> NAME/KEY: DOMAIN
<222> LOCATION: (339)..(355)
<223> OTHER INFORMATION:
<221> NAME/KEY: DOMAIN
<222> LOCATION: (246)..(303)
<223> OTHER INFORMATION:
<221> NAME/KEY: DOMAIN
<222> LOCATION: (198)..(245)
<223> OTHER INFORMATION:
<221> NAME/KEY: DOMAIN
<222> LOCATION: (356)..(400)
<223> OTHER INFORMATION:
<221> NAME/KEY: DOMAIN
<222> LOCATION: (10)..(400)
<223> OTHER INFORMATION:
<221> NAME/KEY: DOMAIN
<222> LOCATION: (340)..(394)
<223> OTHER INFORMATION:
<221> NAME/KEY: DOMAIN
<222> LOCATION: (395)..(439)
<223> OTHER INFORMATION:

<400> SEQUENCE: 1

```
Leu Pro Val Asn Ser Pro Met Asn Lys Gly Asp Thr Glu Val Met Lys
1               5                   10                  15

Cys Ile Val Glu Val Ile Ser Asp Thr Leu Ser Lys Pro Ser Pro Met
            20                  25                  30

Pro Val Ser Gln Glu Cys Phe Glu Thr Leu Arg Gly Asp Glu Arg Ile
        35                  40                  45

Leu Ser Ile Leu Arg His Gln Asn Leu Leu Lys Glu Leu Gln Asp Leu
    50                  55                  60

Ala Leu Gln Gly Ala Lys Glu Arg Ala His Gln Gln Lys Lys His Ser
65                  70                  75                  80

Gly Phe Glu Asp Glu Leu Ser Glu Val Leu Glu Asn Gln Ser Ser Gln
                85                  90                  95

Ala Glu Leu Lys Glu Ala Val Glu Glu Pro Ser Ser Lys Asp Val Met
            100                 105                 110

Glu Lys Arg Glu Asp Ser Lys Ser Ala Glu Lys Ser Gly Glu Ala Thr
        115                 120                 125

Asp Gly Ala Arg Pro Gln Ala Leu Pro Glu Pro Met Gln Glu Ser Lys
    130                 135                 140

Ala Glu Gly Asn Asn Gln Ala Pro Gly Glu Glu Glu Glu Glu Glu Glu
145                 150                 155                 160

Glu Ala Thr Asn Thr His Pro Ala Ser Leu Pro Ser Gln Lys Tyr
                165                 170                 175
```

-continued

```
Pro Gly Pro Gln Ala Glu Gly Asp Ser Glu Gly Leu Ser Gln Gly Leu
            180                 185                 190

Val Asp Arg Glu Lys Gly Leu Ser Ala Glu Pro Gly Trp Gln Ala Lys
        195                 200                 205

Arg Glu Glu Glu Glu Glu Glu Glu Glu Ala Glu Ala Gly Glu Glu
        210                 215                 220

Ala Val Pro Glu Glu Glu Gly Pro Thr Val Val Leu Asn Pro His Pro
225                 230                 235                 240

Ser Leu Gly Tyr Lys Glu Ile Arg Lys Gly Glu Ser Arg Ser Glu Ala
                245                 250                 255

Leu Ala Val Asp Gly Ala Gly Lys Pro Gly Ala Glu Glu Ala Gln Asp
                260                 265                 270

Pro Glu Gly Lys Gly Glu Gln Glu His Ser Gln Gln Lys Glu Glu Glu
            275                 280                 285

Glu Glu Met Ala Val Val Pro Gln Gly Leu Phe Arg Gly Gly Lys Ser
        290                 295                 300

Gly Glu Leu Glu Gln Glu Glu Glu Arg Leu Ser Lys Glu Trp Glu Asp
305                 310                 315                 320

Ser Lys Arg Trp Ser Lys Met Asp Gln Leu Ala Lys Glu Leu Thr Ala
                325                 330                 335

Glu Lys Arg Leu Glu Gly Gln Glu Glu Glu Glu Asp Asn Arg Asp Ser
                340                 345                 350

Ser Met Lys Leu Ser Phe Arg Ala Arg Ala Tyr Gly Phe Arg Gly Pro
            355                 360                 365

Gly Pro Gln Leu Arg Arg Gly Trp Arg Pro Ser Ser Arg Glu Asp Ser
        370                 375                 380

Leu Glu Ala Gly Leu Pro Leu Gln Val Arg Gly Tyr Pro Glu Glu Lys
385                 390                 395                 400

Lys Glu Glu Glu Gly Ser Ala Asn Arg Arg Pro Glu Asp Gln Glu Leu
                405                 410                 415

Glu Ser Leu Ser Ala Ile Glu Ala Glu Leu Glu Lys Val Ala His Gln
                420                 425                 430

Leu Gln Ala Leu Arg Arg Gly
            435
```